United States Patent [19]

Johnson

[11] Patent Number: 5,370,615
[45] Date of Patent: Dec. 6, 1994

[54] BALLOON CATHETER FOR ANGIOPLASTY

[75] Inventor: Kirk Johnson, Miami Lakes, Fla.

[73] Assignee: Cordis Corporation, Miami Lakes, Fla.

[21] Appl. No.: 215,864

[22] Filed: Jan. 18, 1994

Related U.S. Application Data

[63] Continuation of Ser. No. 997,340, Dec. 28, 1992, abandoned.

[51] Int. Cl.$^5$ .............................................. A61M 29/00
[52] U.S. Cl. ...................................... 604/96; 606/194
[58] Field of Search .............................. 606/192, 194; 604/96-101

[56] References Cited

U.S. PATENT DOCUMENTS

| | | | |
|---|---|---|---|
| 4,758,221 | 7/1988 | Jureidini | 604/96 |
| 4,892,519 | 1/1990 | Songer et al. | 604/96 |
| 4,988,356 | 1/1991 | Crittenden et al. | 606/192 |
| 5,042,985 | 8/1991 | Elliot et al. | 604/96 |

FOREIGN PATENT DOCUMENTS 490459  6/1992  European Pat. Off. .............. 604/96

OTHER PUBLICATIONS

Design of Machine Elements, M. F. Spotts, Prentice-Hall, Inc., Englewood Cliffs, N.J. 07632, 1985 p. 343.

*Primary Examiner*—Jerome L. Kruter
*Attorney, Agent, or Firm*—Watts, Hoffmann, Fisher & Heinke Co.

[57] ABSTRACT

An improved balloon catheter is disclosed having both the flexibility of a coaxial construction and the advantages of dual lumen construction as well. The proximal section is of relatively rigid dual lumen construction, wherein an inflation lumen and a guidewire lumen extend longitudinally through the proximal section in a generally parallel and side-by-side relationship. A distal section of the balloon catheter is coupled to the distal end of the proximal section and is of a coaxial construction. Near the transition between the two sections, an inner coaxial member defining the distal guidewire lumen is offset from the center of the otherwise coaxial distal section so that the inner coaxial member is substantially aligned with the distal end of the proximal guidewire lumen. The distal and proximal portions of the guidewire lumen are aligned and heat sealed together at the transition between the dual lumen constructed proximal section and the coaxially constructed distal section of the balloon catheter, to provide a continuous guidewire lumen extending through both sections all the way to a balloon mounted near the distal tip of the distal section. In the dual lumen constructed proximal section, the inflation lumen has a generally crescent-shaped cross section. At the transition region, the proximal inflation lumen narrows somewhat to a circular cross section. The proximal inflation lumen communicates with a substantially annular distal inflation lumen defined between the inner wall of an outer coaxial member and the outer wall of an inner coaxial member in the coaxially constructed distal section.

11 Claims, 1 Drawing Sheet

U.S. Patent      Dec. 6, 1994      5,370,615
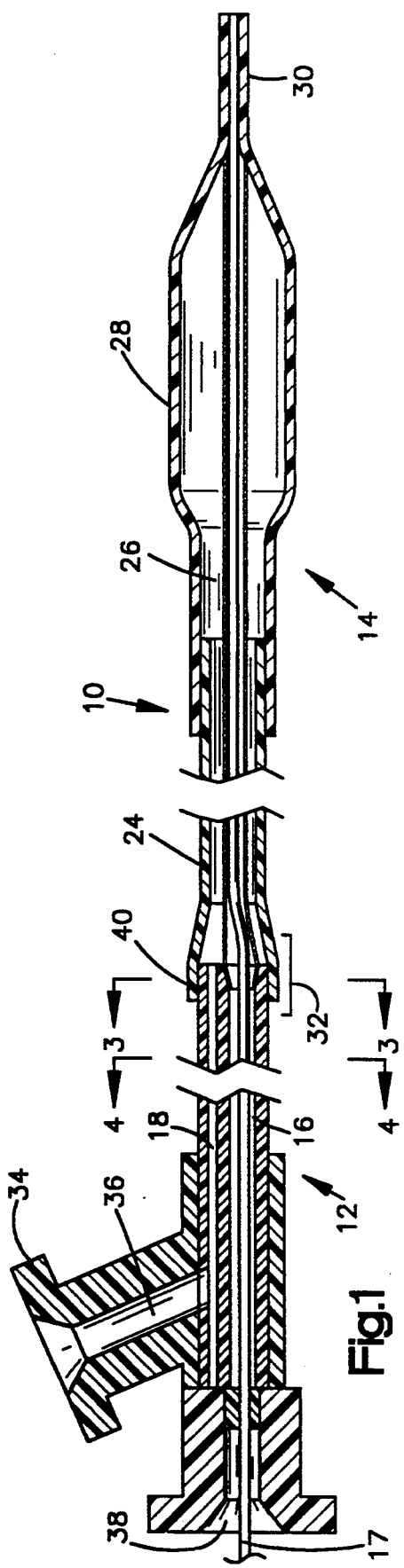
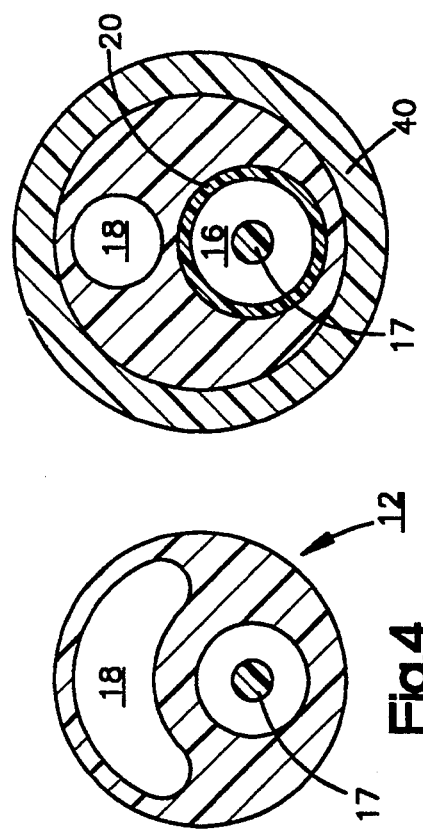
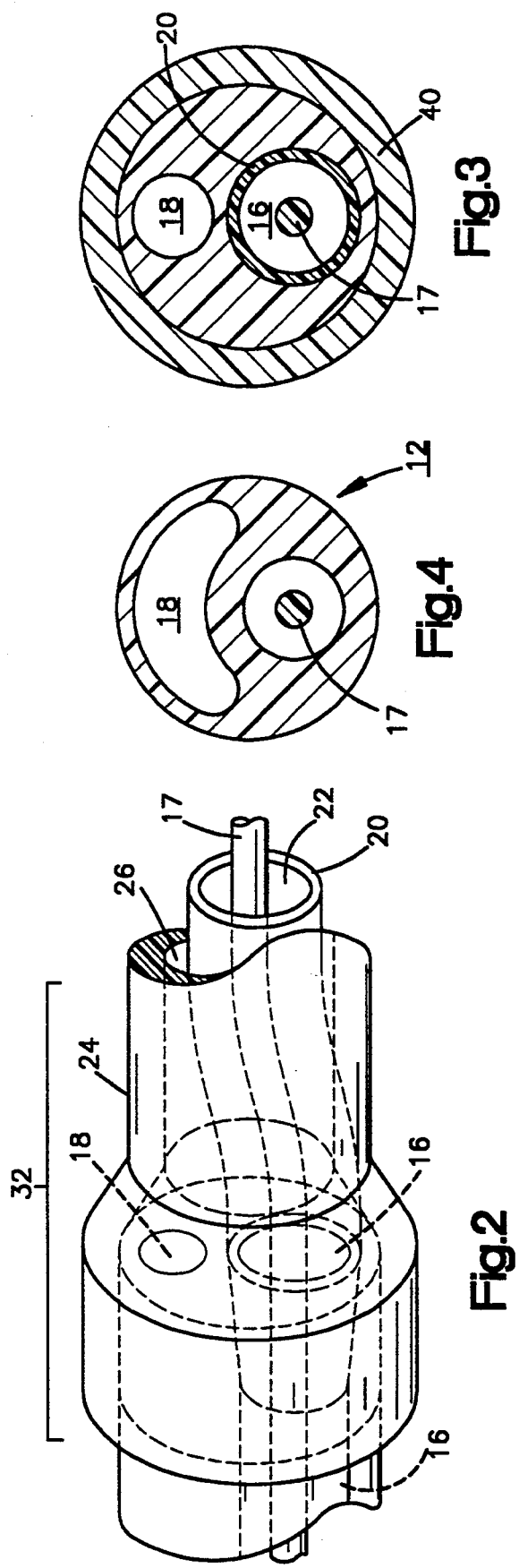

BALLOON CATHETER FOR ANGIOPLASTY

This application is a continuation of U.S. patent application Ser. No. 07/997,340 now abandoned, filed Dec. 28, 1992.

BACKGROUND OF THE ART

1. Technical Field

This invention relates generally to the field of vascular dilatation, such as angioplasty, and more particularly to new and improved balloon catheters for use in such procedures, and to method for making such balloon catheters.

2. Background Art

Cardiac catheterization procedures are well known for diagnosis and therapy of lesions in the cardiovascular system, such as vascular blockage. One such procedure is angioplasty for eliminating or reducing the vascular plaque blockage or constriction in blood vessels associated with providing blood supply to the heart. In such angioplasty procedures, an expandable balloon is introduced into the patient's arterial system and advanced until it is positioned in the region of the blockage or constriction. Once so positioned, the balloon is expanded by inflating it with a liquid. In successful procedures, the expandable balloon presses outwardly against the walls of the blocked artery and expands the artery to a degree to which the artery is either partially or totally re-opened to blood flow.

Typical angioplasty procedures, and components used in practicing the procedures, are now described.

Prior to initiating the angioplasty procedure, a guiding catheter is advanced, typically via the femoral artery into the aorta, with its distal tip is located at or near the ostium, i.e., the location at which the coronary arteries begin to branch from the aorta. Once placed, the guiding catheter acts as a conduit to access the coronary arteries with a balloon guidewire and a balloon catheter.

The guiding catheter is a portion of plastic tubing having a length of about 95 centimeters, and interior diameter of about 0.08 inches, and an outside diameter of about 2.5 millimeters.

The physician performing the procedure threads a balloon catheter onto a balloon guidewire. This operation takes place external to the patient.

The balloon guidewire is a piece of stainless steel and platinum wire, approximately 175 centimeters in length, and about 0.010–0.018 inches in diameter. A soft distal tip of the guidewire can be shaped to form a "J" configuration. This "J" shape facilitates the physician steering the wire by twisting the proximal extremity of the wire while advancing or retracting the wire.

The balloon catheter is an elongated flexible plastic member defining two longitudinal passages and having a balloon located near its distal end. One longitudinal opening defines a balloon guidewire lumen, which forms a sleeve through which the balloon guidewire can be threaded. Another longitudinal passage, an inflation lumen, defines a conduit communicating with the interior of the balloon and through which inflation fluid can be injected to inflate the balloon.

Among the types of balloon catheters is one in which the two longitudinal passages are generally side by side and parallel. This is often referred to as a "dual lumen" balloon catheter. In another type of balloon catheter, the two longitudinal passages are coaxial. This type of balloon catheter is often called a "coaxial lumen catheter". In a coaxial lumen catheter, the balloon guidewire is threaded down the inner passage, which forms the guidewire lumen, and the inflation fluid is injected into the balloon via the outer passage, which forms the inflation lumen.

The physician threads the balloon guidewire through the guidewire lumen in the balloon catheter, leaving a portion of the balloon guidewire extending from the distal end of the balloon catheter and also a portion extending from the proximal end of the balloon catheter.

This assembly, including the balloon guidewire and balloon catheter, is then inserted into the proximal end of the guiding catheter, distal end first. The assembly is inserted until the balloon, which is attached near the distal end of the balloon catheter, is near the distal end of the guiding catheter. At this point, the physician, while maintaining the balloon catheter stationary, pushes on the balloon guidewire to advance it outwardly from the distal end of the guiding catheter.

The balloon guidewire can be steered by appropriate twisting movement by the physician.

The physician steers the balloon guidewire into the chosen one of the coronary arteries, and advances it until its distal end reaches a location of constriction which the physician desires to re-open. Carefully, the physician eases the balloon guidewire through the region of restriction until a portion of the balloon guidewire is on the opposite side of the constriction, relative to the guiding catheter.

With the balloon guidewire held stationary, the physician then advances the balloon catheter. The distal end of the balloon catheter, as it is advanced, will, of course, follow the balloon guidewire which is already in place.

The physician continues to advance the balloon until it is located in the region of the constriction of the artery. With the balloon and its associated catheter held stationary, inflation fluid is injected into the inflation lumen which communicates with the interior of the balloon, causing the balloon to inflate. Inflation of the balloon expands the walls of the artery in the region of constriction and, in successful procedures, re-opens the artery to sufficient blood flow.

Both dual lumen and coaxial lumen catheters have particular advantages and disadvantages.

One advantage of a dual lumen catheter is that it can be relatively stiff, both laterally and axially. This is due to the fact that the two lumens are integrally formed as a portion of the catheter shaft, and are unable to move relative to one another. The rigidity enhances the ability of the physician to push the balloon catheter when desired for advancement of the balloon. Additionally, the dual lumen construction permits direct access to the guidewire lumen through a slit in the side of the catheter, facilitating the guidewire exiting the guidewire lumen on the side, rather than from the end, of the catheter. Such side access to the guidewire lumen is not possible in coaxial lumen catheters, because such access would necessarily require piercing of the outer coaxial inflation lumen in a coaxial design. A further advantage of dual lumen catheters is that there is greater design flexibility in sizing the cross-sectional area of the inflation lumen to optimize inflation fluid flow. The cylindrical inflation lumen made possible in a dual lumen construction has a greater ratio of cross-sectional area to cross-sectional perimeter than does the annular cross-sectioned inflation lumen in the coaxial construction.

Despite all the advantages inherent in the dual lumen construction, the rigidity of the dual lumen design is a disadvantage at the distal end of the catheter. The more rigid dual lumen design is not as compliant as is the coaxial design and therefore is not as facile in tracking tortuous turns in blood vessels through which the catheter is advanced.

Catheters of coaxial lumen design are more compliant and flexible than dual lumen design catheters. This is because the walls of the coaxial lumens can move relative to one another when bending forces are applied to the catheter shaft. This relative movement is not possible in catheters of the dual lumen construction.

It is a general object of the present invention to provide a balloon catheter shaft exhibiting the benefits of both the dual lumen and coaxial constructions, without the disadvantages of either design.

DESCRIPTION OF THE INVENTION

The disadvantages of the prior art catheters are reduced or eliminated by a balloon catheter having a proximal portion constructed in accordance with dual lumen design and a distal portion constructed in accordance with coaxial design.

Transition structure is provided between the two portions for affording respective communication between the guidewire lumens of the two sections and between the inflation lumens of the two sections.

In a more specific embodiment, the distal portion, made in accordance with coaxial design, is about 25 centimeters in length, a length which permits, in an angioplasty procedure, the extension of the distal portion to the occluded area of the blood vessel without requiring extension of the dual lumen proximal portion from the distal end of the guiding catheter.

These and other aspects of the present invention will be understood in more detail by reference to the following detailed description, and to the drawings, in which:

BRIEF DESCRIPTION OF THE DRAWINGS

FIG. 1 is an elevational view, partly in cross section, illustrating the catheter of the present invention;

FIG. 2 is a detail drawing, partly in cross section, illustrating a detail of the embodiment shown in FIG. 1;

FIG. 3 is a cross-sectional view of the catheter taken along the line 3—3 of FIG. 1; and FIG. 4 is a cross-sectional view of the catheter taken along the line 4—4 of FIG. 1.

BEST MODE FOR CARRYING OUT THE INVENTION

An improved balloon catheter 10 is shown in FIG. 1. The balloon catheter 10 includes a proximal section 12 and a distal section 14. Each of the proximal section 12 and distal section 14 includes structure defining two lumens, i.e., a guidewire lumen and an inflation lumen. The proximal section 12 is made in accordance with dual lumen structure, wherein the guidewire lumen and inflation lumen, each not truly circular, extend longitudinally through the proximal section in a generally parallel, side-by-side relationship. The proximal section guidewire lumen is designated by reference character 16. The proximal inflation lumen is designated by reference character 18 in FIG. 1.

The guidewire is designated by the reference character 17.

The distal section 14 is made in accordance with a coaxial lumen design. The distal section 14 includes an inner coaxial member 20 which is generally cylindrical in shape and which defines therewithin a distal guidewire lumen 22. The distal section also includes an outer coaxial member 24. The outer coaxial member 24 is also cylindrical in shape and has a larger diameter than does the inner coaxial member 20. The outer coaxial member 24 surrounds the inner coaxial member 20. The space between the outer wall of the inner coaxial member and the inner wall of the outer coaxial member 24 defines a distal inflation lumen 26 (see FIG. 2). The distal inflation lumen 26 is generally annular in cross section.

The distal inflation lumen 26 communicates with the interior of a balloon 28 located near the distal end of the distal section 14. The balloon 28, when inflated with inflation fluid, expands to apply therapeutic outward pressure against the interior walls of an occluded blood vessel in which the balloon 28 is positioned.

At the distal end 30 of the distal section 14, the walls of the balloon narrow and contact the outer surface of the inner coaxial member about its circumference. Those contacting surfaces of the balloon and of the inner coaxial member are heat-sealed together, or are sealed about the circumference of the inner coaxial member by adhesive.

Over a transition region 32, the distal guidewire lumen is coupled to and communicates with the proximal guidewire lumen, and the distal inflation lumen is coupled to and communicates with the proximal inflation lumen.

A hub 34 defines a balloon inflation port 36 which communicates with the proximal inflation lumen to provide a means whereby balloon inflation fluid can be selectively injected into, or removed from, the balloon in order to govern its degree of inflation.

The distal section 14 is preferably at least about 25 centimeters in length. The selection of such a length for the distal section allows the distal section to protrude from the end of a guiding catheter to a degree sufficient to position the balloon in the occluded portion of the blood vessel which is to be treated, without necessitating the protrusion of any portion of the proximal section of the balloon catheter from the distal end of the guiding catheter.

The left-hand end of the proximal guidewire lumen, as shown in FIG. 1, terminates in a balloon guidewire port 38. The balloon guidewire can be inserted into the port 38 and advanced through both the proximal guidewire lumen and the distal guidewire lumen, to the degree desired by the physician.

The transition region is approximately 0.060 inch in length. The wall thicknesses of the inner coaxial member and outer coaxial member are approximately 0.002–0.003 inches. The total outside diameter of the balloon catheter, other than in the region of the balloon itself, is about 0.040 inch. Both the distal section and the proximal section of the balloon catheter are made of plastic, preferably nylon.

FIGS. 2 and 3 illustrate in more detail the transition region 32 between the dual lumen construction of the proximal section and the coaxial construction of the distal section. FIG. 2 is an elevational view, partly in cross section, and partly broken away, while FIG. 3 is a cross-sectional view taken perpendicular to the catheter through the transition region 32, along the line 3—3.

FIG. 2 illustrates that the end of the distal section which faces the proximal section is flared, as indicated at reference character 40 in FIG. 1 such that, over the transition region, the inner surface of the distal section overlaps the outer surface of the proximal section, about substantially the entirety of the outer surface of the proximal section. Additionally, the distal end of the portion of the guidewire lumen associated with the proximal section is flared as well. Over the portion of overlap, the outer surface of the proximal section and the inner surface of the distal section are heat-sealed together, forming a liquid-tight seal. Alternatively, the outer surface of the proximal section and the inner surface of the distal section can be sealed with adhesive.

The proximal guidewire lumen 16 as mentioned above, is of a circular cross section. The diameter of the proximal guidewire lumen 16 is approximately 0.018 inches. The proximal section 12 is heat fused, at the transition region 32, to the proximal end of the inner coaxial member 20. The inner coaxial member 20 is of circular cross section and has an inside diameter substantially the same as that of the proximal guidewire lumen 16.

At and very near the transition region 32, the inner coaxial member 20 is offset from the center of the distal section so that is aligns with the distal end of the proximal guidewire lumen, to which it is heat sealed. Note, however, that at no point is the inner coaxial member 20 actually adhered to the inner wall of the outer coaxial member 24. Rather, some slight space between the outer wall of the inner coaxial member and the inner wall of the outer coaxial member still exists, even over the transition region 32. As the inner coaxial member extends from the transition region to the distal end of the catheter, it quickly reverts to its coaxially central location within the coaxially constructed distal section 14. It is only at and very near the transition region 32 that the inner coaxial member is offset from the center of the distal section of the catheter.

The proximal inflation lumen has a cross sectional shape which is approximately that of a crescent. The membrane between the two lumens in the proximal section is about 0.003 inches in thickness.

The reason for utilizing a crescent-shaped inflation lumen in the proximal section, which has dual lumen construction, is to maximize the cross sectional area of the inflation lumen. Maximizing the cross sectional area of the inflation lumen minimizes friction which tends to inhibit the flow of the inflation fluid.

It is desirable to deflate the balloon very quickly should complications arise during the angioplasty procedure. A way of facilitating the rapid deflation of the balloon is to provide an inflation lumen having maximum cross-sectional area and a minimum ratio of cross sectional area to cross-sectional perimeter. The basic approach in the dual lumen construction of the proximal section 12 is to provide a guidewire lumen having just enough cross sectional area to freely accommodate the guidewire, and to dedicate as much as possible of the remaining cross sectional area of the proximal section 12 to the inflation lumen.

FIG. 4 is a cross-sectional view of the proximal portion of the catheter, in which the inflation lumen has an approximately crescent-shaped configuration.

Due to manufacturing considerations, however, the proximal inflation lumen, near the distal end of the proximal section 12, and the transition region 32, is heat fused over a very short distance in the transition region, into an approximately circular cross section having a diameter of about 0.013 inches. This transition of the proximal inflation lumen into a very short circular cross section is preferred because a simple circular cross sectioned mandrel can be used to form the inflation lumen near the distal tip of the proximal section 12.

It might be feasible to manufacture a proximal section wherein the inflation lumen has the desired crescent-shaped cross section over its entire length, but such a fabrication is believed to require a crescent mandrel. Manufacture and use of a crescent-shaped mandrel having dimensions as small as those required in this type of structure (the outside diameter of the entire catheter is only about 0.040 inches) presently renders impractical the use of such a crescent-shaped mandrel to effect an inflation lumen having a crescent shape over the entire length of the proximal section 12. The reduced cross-sectional area at this region does not significantly reduce fluid flow because it is only 0.060 long.

FIG. 3 illustrates the cross-sectional configuration of the catheter in the very short heat fused region, in which the inflation lumen takes on a circular cross section before opening out into the larger cross section inflation lumen of the coaxial distal section.

While the present invention has been described in some detail, it is to be understood that those of ordinary skill may make certain additions or modifications to, or deletions from, the disclosed preferred embodiment, without departing from the spirit or scope of this invention, as defined in the appended claims.

I claim:

1. A balloon catheter comprising:
   a. a distal catheter section including a balloon and structure defining an inner guidewire lumen that extends through the balloon and an outer inflation lumen coaxial with the inner lumen for inflating the balloon;
   b. a proximal section having structure defining a guidewire lumen and inflation lumen in side-by-side relation to each other and further including structure to allow a guidewire to be inserted into the guidewire lumen and fluid to be injected into the inflation lumen; and
   c. A transition catheter section connecting said proximal and said distal sections, said transition section having structure connecting said proximal section guidewire lumen with said distal section guidewire lumen, and structure connecting said proximal section inflation lumen with said distal section inflation lumen, said distal section outer inflation lumen being coaxial with said distal section guidewire lumen over said distal section from said transition section to a location near said distal end of said distal section.

2. The balloon catheter of claim 1 wherein:
   said distal section includes an elongated portion between the balloon and the proximal catheter section that is at least 25 centimeters in length.

3. A balloon catheter comprising:
   a. a proximal catheter section having structure defining a guidewire lumen and an inflation lumen extending longitudinally through said proximal catheter section in a substantially parallel, side-by-side relationship;
   b. A distal catheter section connected to the proximal catheter section including an inner member defining a longitudinal guidewire lumen extending through said distal section in fluid communication with the guidewire lumen of the proximal catheter section and an outer member coaxially surrounding said inner member over the distal section and defining a longitudinally extending inflation lumen between the outer surface of said inner member and the inner surface of said outer member in fluid communication with the inflation lumen of said proximal catheter section; and c. a flexible balloon attached to the outer member of the distal catheter section at a proximal end of the balloon and attached to the inner member of the distal catheter section at a distal end of the balloon.

4. The balloon catheter of claim 3, wherein:
said proximal section and said distal section are connected in a transition region in which said inner member of said distal section a guidewire lumen defining portion of said proximal catheter section.

5. The balloon catheter of claim 4, wherein:
said outer ember of said distal section engages an inflation lumen defining portion of said proximal catheter section in said transition region to allow fluid for inflating the balloon to flow from the proximal to distal sections.

6. The balloon catheter of claim 4, wherein an end of said distal section facing said proximal section includes an outwardly flared portion that overlaps and contacts, over said transition region, substantially an entire outer surface of said proximal section.

7. The balloon catheter of claim 6, wherein said flared portion of said distal section is heat sealed to said outer surface of said proximal section.

8. The balloon catheter of claim 6, wherein said flared portion of said distal section is sealed to the outer surface of said proximal section by means of adhesive.

9. A balloon catheter comprising:
a. an elongated distal section including a balloon and an inner member defining an inner guidewire lumen that extends through the balloon and an outer member defining an outer inflation lumen coaxial with the inner lumen over the distal section for inflating the balloon;
b. an elongated proximal section having structure defining a guidewire lumen and inflation lumen that extend next to each other to openings in a distalmost end of the elongated proximal section;

c. a coaxial transition region connecting said proximal section and said distal sections, said transition region having structure connecting said proximal section guidewire lumen with said distal section guidewire lumen being coaxial with the invention lumen, and structure connecting said proximal section inflation lumen with said distal section inflation lumen; and
d. input means connected to the proximal section of the catheter for injecting fluid for inflating the balloon into the inflation lumen and for inserting a guidewire into the guidewire lumen.

10. A balloon catheter for use in vascular dilatation procedures, said balloon catheter comprising:
a. a distal catheter section including a balloon and an inner member defining an inner guidewire lumen that extends through the balloon and an outer member defining an outer inflation lumen coaxial with the inner lumen over said distal section from the transition location to the distal end balloon;
b. a proximal shaft section having structure defining a guidewire lumen and inflation lumen in side-by-side relation to each other and further including structure to allow a guidewire to be inserted into the guidewire lumen and fluid to be injected into the inflation lumen; and
c. a transition catheter section connecting said proximal and said distal sections, said transition section having structure connecting said proximal section guidewire lumen with said distal section guidewire lumen, and structure connecting said proximal section inflation lumen with said distal section inflation lumen, said transition section being displaced proximally along the balloon catheter shaft with respect to the balloon at a distance sufficiently proximal to said balloon such that, during a vascular dilatation procedure, said distal section of said balloon catheter does not protrude from the distal end of a guiding catheter in which said balloon catheter is located.

11. The balloon catheter of claim 10, wherein:
said transition region is located about at least 25 centimeters proximal to said balloon.

* * * * *